United States Patent [19]
Umezawa et al.

[11] Patent Number: 4,634,688
[45] Date of Patent: Jan. 6, 1987

[54] 3'-FLUORO-3'-DEOXYKANAMYCIN A

[75] Inventors: Hamao Umezawa; Sumio Umezawa, both of Tokyo; Tsutomu Tsuchiya, Yokohama; Yoshiaki Takahashi, Tokyo, all of Japan

[73] Assignee: Zaidan Hojin Biseibutsu Kagaku Kenkyu Kai, Japan

[21] Appl. No.: 758,819

[22] Filed: Jul. 25, 1985

[30] Foreign Application Priority Data

Aug. 2, 1984 [JP] Japan ................................. 59-161615

[51] Int. Cl.$^4$ ........................ A61K 31/71; C07H 15/22
[52] U.S. Cl. ....................................... 514/41; 536/13.7
[58] Field of Search ........................... 536/13.7; 514/41

[56] References Cited
U.S. PATENT DOCUMENTS 4,349,666  9/1982  Umezawa et al. ................. 536/13.7
4,357,466  11/1982 Umezawa et al. ................. 536/13.7

Primary Examiner—Johnnie R. Brown
Assistant Examiner—Elli Peselev
Attorney, Agent, or Firm—Larson and Taylor

[57] ABSTRACT

A new compound, 3'-fluoro-3'-deoxykanamycin A is now provided, which is active against gram-negative and gram-positive bacteria, including kanamycin-resistant strains of bacteria and is useful as antibacterial agent for therapeutic treatment of bacterial infections. This new compound is produced by a process comprising reacting a 6-azido-2,4-di-O-protected-3,6-dideoxy-3-fluoro-α-D-glucopyranosyl bromide with the 4-hydroxyl group of a 6-O-(2'-O-protected-3'-N-protected-3'-amino-4',6'-di-O-protected-3'-deoxy-α-D-glucopyranosyl)-1,3-bis-N-protected-2-deoxystreptamine, reducing the azido group of the resulting reaction product into an amino group, and removing the remaining protective groups from the reduction product.

2 Claims, 1 Drawing Figure

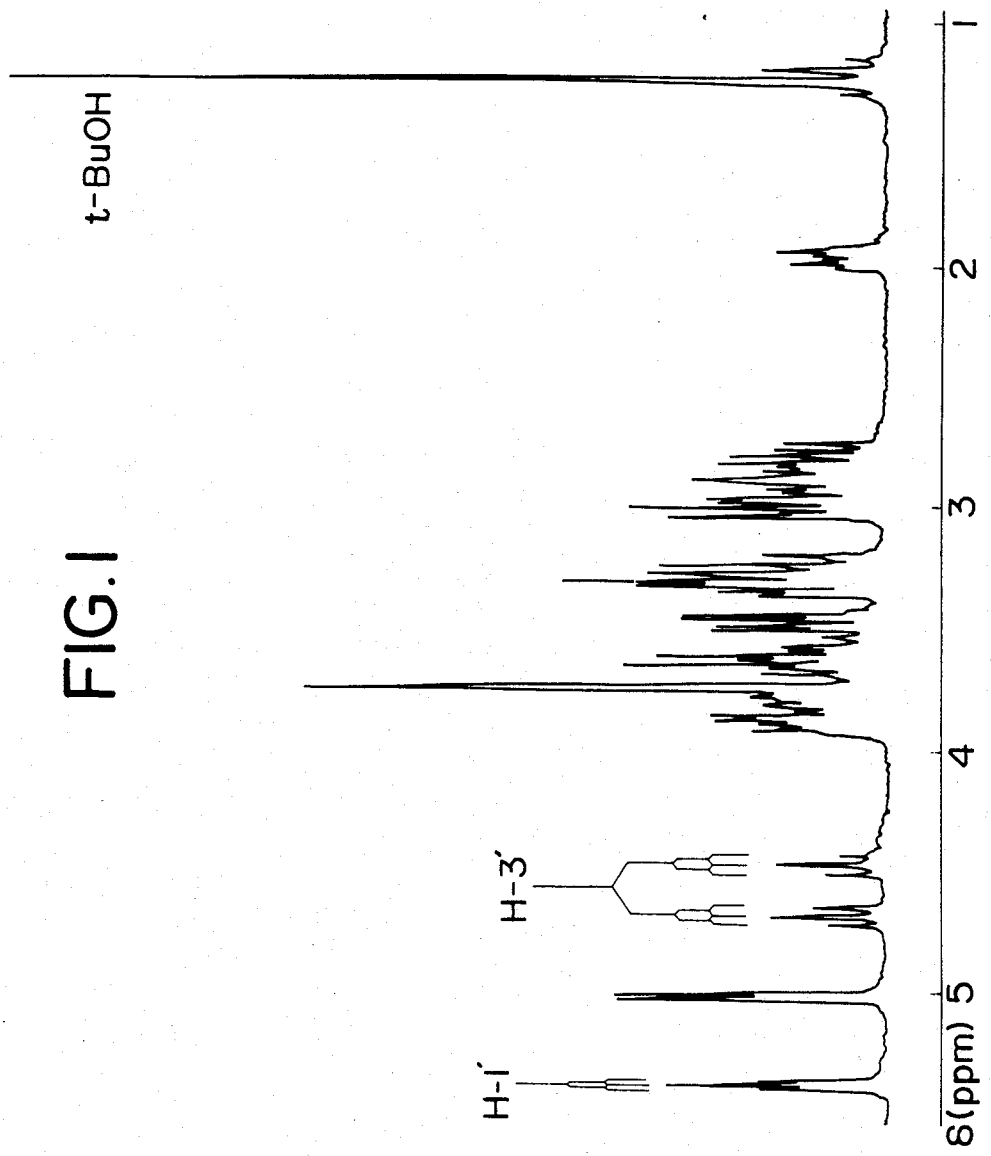

3'-FLUORO-3'-DEOXYKANAMYCIN A

SUMMARY OF THE INVENTION

This invention relates to 3'-fluoro-3'-deoxykanamycin A which is a new semi-synthetic aminoglycosidic antibiotic and which is a new compound exhibiting a high antibacterial activity against a variety of kanamycin-sensitive bacteria and kanamycin-resistant bacteria and is useful as an antibacterial agent. This invention also relates to a pharmaceutical composition containing 3'-fluoro-3'-deoxykanamycin A as active ingredient.

BACKGROUND OF THE INVENTION

Various deoxy derivatives of kanamycins A, B and C are already known as the semi-synthetic aminoglycosidic antibiotics which have been derived from kanamycins A, B and C. These known deoxy derivatives of kanamycins have usefully high antibacterial activities, but the antibacterial spectra of these known deoxykanamycin derivatives are of varying ranges. Besides, the known deoxykanamycin derivatives are possible to be inactive against such new resistant strains of bacteria which will possibly occur in future. Accordingly, it is always requested that new, antibacterial compounds having any more excellent properties than the known antibacterial compounds should be created and provided for uses in therapeutic treatment of bacterial infections. We, the present inventors, had an expectation that if we would succeed in synthetizing such a new kanamycin A derivative having the 3'-hydroxyl group replaced by a fluoro group, namely a kanamycin A derivative identifiable as 3'-fluoro-3'-deoxykanamycin A, this new compound should be active against some kanamycin-resistant strains of bacteria which are already known and also against some another resistant strains which will possibly occur in future. With such expectation, we have made our efforts to synthetize 3'-fluoro-3'-deoxykanamycin A with starting from kanamycin A, but we have not yet get a success in synthetizing such new compound with starting from kanamycin A itself. This is mainly because kanamycin A contains three adjacent, 2'-, 3'- and 4'-hydroxyl groups in the molecule thereof, leading to a large difficulty that only the 3'-hydroxyl group can hardly be replaced by a fluoro group, as far as the synthesis of 3'-fluoro-3'-deoxykanamycin A is to be achieved with using kanamycin A as the starting material. With kanamycin B, on the other hand, it was feasible to produce 3'-iodo- or 3'-bromo-derivative thereof with starting from kanamycin B when such a synthetic process of producing 3'-deoxykanamycin B is followed, wherein kanamycin B is used as the starting compound and firstly converted into a penta-N-protected-2'',4'',6''-tri-O-protected-kanamycin B derivative, of which the 3'-hydroxyl group is then alkylsulfonylated or arylsulfonylated; and wherein the resultant alkylsulfonylated or arylsulfonylated 3'-hydroxyl group of the N,O-protected kanamycin B is further reacted with an alkali metal iodide or bromide to give a 3'-iodo- or 3'-bromo-N,O-protected kanamycin B derivative which may subsequently be converted either into 3'-iodo- or 3'-bromo-3'-deoxykanamycin B through the removal of all the residual amino-protecting and hydroxyl-protecting groups therefrom or into 3'-deoxykanamycin B through the reduction of the 3'-halo group into a hydrogen atom and the removal of the residual amino-protecting and hydroxyl-protecting groups therefrom (see Japanese patent publication No. 876/82, Example 1; U.S. Pat. No. 3,929,762 U.K. Pat. No. 1,426,910). Through our experiments, however, it has been confirmed that any 3'-halogenated derivative of kanamycin A could not be produced even if the above-mentioned process of producing the 3'-iodo- or 3'-bromo-derivative of kanamycin B as disclosed in the specification of said Japanese patent publication No. 876/82 or the U.S. Pat. No. 3,929,762 is applied to kanamycin A. Besides, in the course of our researches in an attempt to exploit a route for the synthesis of 3'-deoxykanamycin A from kanamycin A, we have realized that kanamycin A is remarkedly different from kanamycin B in their behaviors to chemical reagents, and hence, due to the unique behaviors of the kanamycin A and particularly of the 2'-, 3'- and 4'-hydroxyl groups of kanamycin A, we had to develope such a method for synthesis of 3'-deoxykanamycin A which comprises some steps and procedures entirely different from those involved in the previously exploited process of synthetizing 3'-deoxykanamycin B from kanamycin B (see, for example, Japanese patent application first publication "Kokai" Nos. 68698/81; 118097/81 and 152497/81, U.S. Pat. No. 4,349,666; U.K. Pat. No. 2,061,942B, U.S. Pat. No. 4,357,466; U.K. Pat. No. 2,064,518B, U.S. Pat. No. 4,337,336; U.K. Pat. No. 2,070,007B, U.S. Pat. No. 4,359,572; U.K. Pat. No. 2,075,010B).

Accordingly, we have now made another approach to the synthesis of 3'-fluoro-3'-deoxykananycin A, and as a result of our researches we have now succeeded in synthetizing 3'-fluoro-3'-deoxykanamycin A first time by a synthetic process wherein 3-deoxy-3-fluoro-1,2:5,6-di-O-isopropylidene-α-D-glucofuranose, a known compound disclosed in the "Journal of Organic Chemistry" Vol. 43, No. 6, pages 1090–1092 (1978), is used as the starting compound and is subjected to a series of reaction steps as described hereinafter and illustrated with reference to Examples 1 to 3 given hereinafter. We have now further found that the 3'-fluoro-3'-deoxykanamycin A as synthetized by us is a new compound exhibiting antibacterial activities against gram-negative and gram-positive bacteria, including kanamycin-resistant bacterial strains.

DETAILED DESCRIPTION OF THE INVENTION

According to a first aspect of this invention, therefore, there is provided 3'-fluoro-3'-deoxykanamycin A represented by the formula (I)

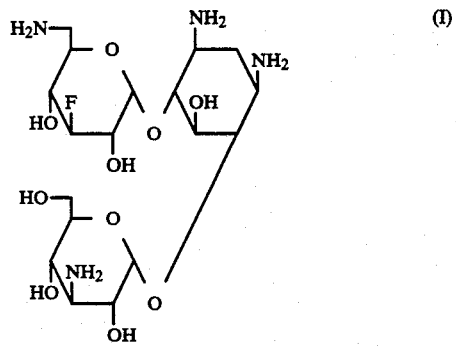

or a pharmaceutically acceptable acid addition salt thereof.

3'-Fluoro-3'-deoxykanamycin A of this invention is a basic substance which is in the form of a colorless powder having no definite melting point and gives a specific optical rotation $[\alpha]_D^{25} +116°$ (c 0.5, water) and an $^1$H-N.M.R. absorption peaks as briefed in Example 3 hereinafter and shown in FIG. 1 of the accompanying drawing.

With reference to the accompanying drawing:

FIG. 1 shows a proton nuclear magnetic resonance ($^1$H-N.M.R.) absorption spectrum of 3'-fluoro-3'-deoxy kanamycin A (in 20% deutero-ammonia in deutero-water, with tetramethylsilane as internal standard).

The new compound of the formula (I) according to this invention is usually obtained from the process for the production thereof in the form of a free base, a hydrate or a carbonate. 3'-Fluoro-3'-deoxykanamycin A may be converted into a pharmaceutically acceptable, non-toxic acid addition salt thereof in a known manner by reacting with a pharmaceutically acceptable inorganic acid such as hydrochloric acid, sulfuric acid, phosphoric acid, nitric acid and the like; or a pharmaceutically acceptable organic acid such as acetic acid, malic acid, citric acid, ascorbic acid methanesulfonic acid and the like.

According to a second aspect of this invention, there is provided an antibacterial composition comprising an antibacterially effective amount of 3'-fluoro-3'-deoxykanamycin A or a pharmaceutically acceptable acid addition salt thereof as the active ingredient, in association with a pharmaceutically acceptable liquid or solid carrier or vehicle for the active ingredient.

The minimum inhibitory concentrations (MIC., mcg/ml) of 3'-fluoro-3'-deoxykanamycin A of this invention against a variety of bacteria were determined by a standard serial dilution method, and the antibacterial spectrum of 3'-fluoro-3'-deoxykanamycin A (abbreviated as 3'-F-kanamycin A) (the free base) is shown in Table 1 below. For comparison, the antibacterial spectra of kanamycin A and 3'-deoxykanamycin A are also shown in Table 1.

Apart from the method necessary for the preparation of the starting compounds as employed, the production of 3'-fluoro-3'-deoxykanamycin A may be achieved by a process comprising three reaction stages. Thus, a process for the production of 3'-fluoro-3'-deoxykanamycin A may comprise a step (i) of reacting a 6-azido-2,4-di-O-protected-3,6-dideoxy-3-fluoro-α-D-glucopyranosyl bromide of the formula (II)

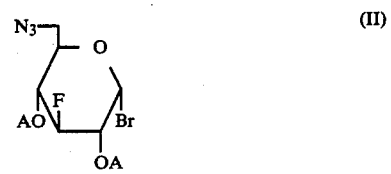

wherein A is a hydroxyl-protecting group, preferably a benzyl group, with the 4-hydroxyl group of a 6-O-(2'-O-protected-3'-N-protected-3'-amino-4',6'-di-O-protected-3'-deoxy-α-D-glucopyranosyl)-1,3-bis-N-protected-2-deoxystreptamine of the formula (III)

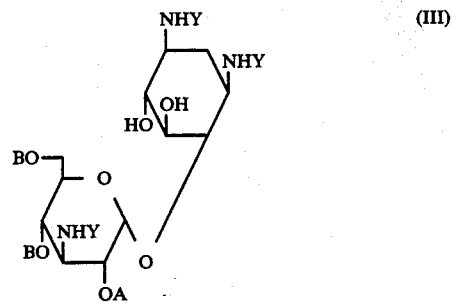

wherein Y is an amino-protecting group, A is a hydroxyl-protecting group, and every group B is a monovalent hydroxyl-protecting group, either same as or different from the group A, or a pair of two groups B together form a di-valent hydroxyl-protecting group selected from an alkylidene group and a cycloalkylidene group, to produce a condensation product of the formula (IV)

TABLE 1

| | M.I.C. (mcg/ml) | | |
|---|---|---|---|
| Test organisms | 3'-F—kanamycin A (this invention) | Kanamycin A (comparative) | 3'-deoxykanamycin A (comparative) |
| Staphylococcus aureus 209P | 1.56 | 1.56 | 3.12 |
| Staphylococcus aureus Smith | 0.78 | 1.56 | 1.56 |
| Micrococcus luteus PCI 1001 | 6.25 | 6.25 | 25 |
| Bacillus subtilis PCI 219 | 0.39 | 0.39 | 0.78 |
| Escherichia coli NIHJ | 0.78 | 0.78 | 0.78 |
| Escherichia coli K-12 | 1.56 | 0.78 | 3.12 |
| Escherichia coli K-12 ML 1629 | 3.12 | >100 | 6.25 |
| Escherichia coli K-12 ML 1630 | 6.25 | >100 | 12.5 |
| Escherichia coli K-12 ML 1410 R 81 | 6.25 | >100 | 6.25 |
| Escherichia coli K-12 JR 66/W 677 | 50 | >100 | >100 |
| Mycobacterium 607 | 0.78 | 0.78 | 1.56 |
| Pseudomonas aeruginosa A3 | 0.39 | 3.12 | 0.39 |
| Pseudomonas aeruginosa No. 12 | 3.12 | 25 | 3.12 |
| Pseudomonas aeruginosa H-11 | 6.25 | 100 | 12.5 |
| Pseudomonas aeruginosa TI-13 | 3.12 | 25 | 6.25 |
| Pseudomonas aeruginosa 99 | 6.25 | >100 | 6.25 |

As will be clear from the results of Table 1, 3'-fluoro-3'-deoxykanamycin A is active against the kanamycin A-resistant bacteria, like 3'-deoxykanamycin A, but it can show a higher antibacterial activity than that of 3'-deoxykanamycin A, not only against the resistant strains of Escherichia coli but also against Pseudomonas aeruginosa. In account of this, it may be said that the 3'-fluorination imparts kanamycin A with a higher antibacterial activity than the 3'-deoxygenation.

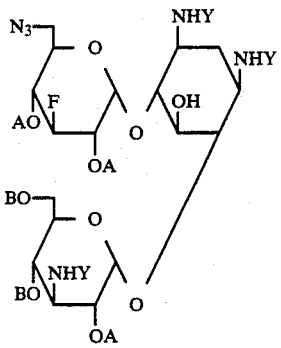

(IV)

wherein A, B and Y are each as defined above; a step (ii) of reducing the azido group (—N₃) of the condensation product of the formula (IV) into an amino group (—NH₂), and a step (iii) of removing the remaining hydroxyl-protecting groups and amino-protecting groups from the amination product as obtained in the step (ii), thereby producing 3'-fluoro-3'-deoxykanamycin A, namely the final compound of the formula (I).

The starting compound of the formula (II) as above may be prepared by using such methyl 6-azido-3,6-dideoxy-3-fluoro-α- and β-D-glucopyranosides as made by the method described in the Example 1, (a) to (d) given hereinafter, protecting the two hydroxyl groups of the methyl 6-azido-3,6-dideoxy-3-fluoro-α- and β-D-glucopyranosides with a known hydroxyl-protecting group such as benzyl group, reacting the resultant methyl 6-azido-2,4-di-O-protected-3,6-dideoxy-3-fluoro-α- and β-D-glucopyranosides with acetic anhydride to produce 1-O-acetyl-6-azido-2,4-di-O-protected-3,6-dideoxy-3-fluoro-α- and β-D-glucopyranoses, which are then brominated by reaction with titanium tetrabromide (see Example 1, (e) to (g) given hereinafter).

The compound of the formula (III) to be reacted with the starting compound of the formula (II) may be prepared by protecting with a known amino-protecting group the 1-, 3- and 3'-amino groups of a known compound, 6-O-(3'-amino-3'-deoxy-α-D-glucopyranosyl)-2-deoxystreptamine, and then protecting the 2'-hydroxyl group of the resulting 1,3,3'-tri-N-protected derivative of said known compound with a known hydroxyl-protecting group via three steps to produce a 6-O-(2'-O-protected-3'-N-protected-3'-amino-3'-deoxy-α-D-glucopyranosyl)-1,3-bis-N-protected-2-deoxystreptamine (see the "Bulletin Chemical Society of Japan" Vol. 42, pages 533-537 (1969)), and further protecting the 4'- and 6'-hydroxyl groups of the latter deoxystreptamine compound with two mono-valent known hydroxyl-protecting groups, respectively, or with a di-valent known hydroxyl-protecting group, for example, an alkylidene group, preferably isopropylidene group or a cycloalkylidene group, preferably a cyclohexylidene group (see Example 2 given hereinafter).

In the process for the production of the compound (I) of this invention, the step of reacting the compound of the formula (II) with the compound of the formula (III) by condensation reaction may be carried out in the presence of mercuric cyanide as a condensation catalyst in an anhydrous organic solvent such as a chlorinated hydrocarbon, preferably dichloromethane at an elevated temperature of e.g. 80° to 100° C. under heating. The azido group (—N₃) of the condensation product of the formula (IV) so formed may be reduced into an amino group by a catalytic reduction with hydrogen in the presence of a palladium catalyst. The reduction of the azido group may be effected concurrently to the removal of the remaining amino-protecting groups, if desired. The step of removing the remaining hydroxyl-protecting groups and amino-protecting groups may be achieved in a known manner according to a conventional deprotection technique as properly chosen depending on the kinds of the protective groups to be cleaved and may optionally be effected in two or more separate stages. For instance, the reaction of the compound of the formula (II) with the compound of the formula (III) by condensation, as well as the reduction of the azido group may be performed in a manner similar to such procedures as illustrated in the specification of U.S. Pat. No. 3,929,761 in which a method for synthesis of 3'-doexykanamycin A is described.

The reaction solution as obtained from the aforesaid step of removing the remaining protective groups may then be concentrated to dryness and the solid residue obtained may be taken up into a volume of water, followed by chromatographying the resultant aqueous solution containing the 3'-fluoro-3'-deoxykanamycin A product in a column of a gel filtration agent, CM-Sephadex C-25 as developed with aqueous ammonia to effect the isolation and purification of the desired 3'-fluoro-3'-deoxykanamycin A of the formula (I).

For estimation of acute toxicity of 3'-fluoro-3'-deoxykanamycin A, this new compound was administered intravenously or intraperitoneously at a dosage of 150 mg/kg into five mice, all mice did not shown any abnormal symptons and survived for 3 weeks, revealing that the new compound under test is of a low toxicity.

The antibacterial composition of this invention may be formulated into suitable forms for oral, parenteral or intrarectal administration. Composition in the form of injectable solution may contain 0.1% to 10.0% by weight of the compound (I) as active ingredient, and also one or more of a pH-adjuster, buffer, stabilizer, excipient, local anesthetics and an additive for rendering the solution isotonic. The injectable solution may be prepared to be adapted for subcutaneous, intramuscular or intravenous injection by any conventional pharmaceutical technique. Solid composition for oral administration which may be in the form of tablets, coated tablets, granules, powder and capsules, may contain excipients for the active ingredient, and if required, other additives, including disintegrators, lubricants, colorants, flavors and the like. The proportion of the active compound to the carrier may be at a ratio of 1:1 to 1:100 by weight and may usually be chosen appropriately depending on the form of the orally administrable formulation prepared. Suppository formulations may contain excipients and, if necessary, surfactant and lubricants additionally to the active compound.

The optimum dosage of the new compound (I) administered will, of course, depend on the mode of administration and the treatment aimed. For men, the unit dosage for injections generally contains from 50 mg to 200 mg of the compound (I), which may be administered intravenously or intramuscularly in divided doses one or more times per day. The new compound of the formula (I) used in the composition of this invention may be administered orally to an adult person at a dosage of 50 mg to 200 mg once a day.

This invention is now illustrated with reference to the following Examples 1 to 3. Example 1 shows the preparation of a starting compound of the formula (II), Example 2 shows the preparation of a reagent compound of the formula (III), and Example 3 illustrates the production of the desired compound of the formula (I) of this invention.

EXAMPLE 1

(a) Synthesis of 3-deoxy-3-fluoro-1,2-O-isopropylidene-α-D-glucofuranose (Compound No. 2) from 3-deoxy-3-fluoro-1,2:5,6-di-O-isopropylidene-α-D-glucofuranose (Compound No. 1)

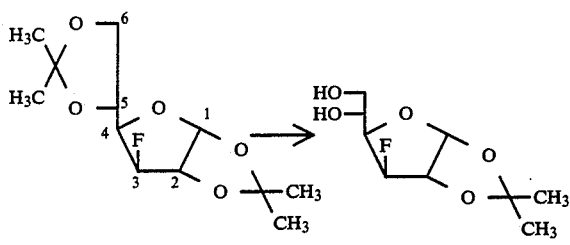

(Compound No. 1)    (Compound No. 2)

Compound No. 1 of the formula as above (40.05 g, liquid) (see Timothy J. Tewson and Michael J. Welch, "J. Org. Chem." 43, (6), 1090–1092 (1978)) was mixed with 600 ml of a mixture of acetic acid and water (1:4 by volume), followed by stirring the whole mixture at 40° C. for 8 hours to effect a partial hydrolysis of Compound No. 1. The resulting reaction solution has become homogenous and then concentrated under reduced pressure, the syrupy material obtained was taken up into water and the aqueous solution as formed was passed through a column of 330 ml of an ion-exchange resin "Dowex" 1×2 (OH cycle) for removal of the remaining acetic acid from said aqueous solution. The effluent solution coming from the resin column was concentrated to give the titled Compound No. 2 as a colorless syrupy substance. Yield 33.30 g (98%).

(b) Synthesis of 3-deoxy-3-fluoro-1,2-O-isopropylidene-6-O-tosyl-α-D-glucofuranose (Compound No. 3)

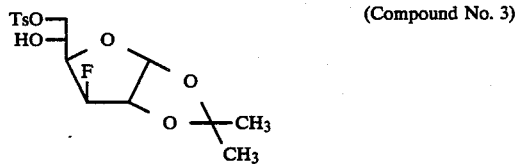

(Compound No. 3)

where Ts denotes a tosyl group herein and hereinafter, unless otherwise stated.

Compound No. 2 (31.55 g) obtained in the above procedure (a) was dissolved in 600 ml of pyridine, to which was then added 32.5 g of tosyl chloride under ice-cooling. The resulting mixture was kept at room temperature overnight (for 19 hours) to effect the tosylation. The reaction solution was diluted with 19 ml of water, left to stand for 0.5 hour and then concentrated to give a brown colored syrup, which was subsequently taken up into 2 liters of chloroform. The solution in chloroform was washed with aqueous 5% potassium hydrogen sulfate, with aqueous 5% sodium hydrogen carbonate and then with water, dried over anhydrous sodium sulfate and concentrated under reduced pressure to give a brown colored syrupy substance. This substance was purified by silica gel column chromatography on a column of 3000 ml of silica gel (as developed with benzene-ethyl acetate (5:1) as eluent) to afford the titled Compound No. 3 as a faintly yellow colored syrup. Yield 41.40 g (76.4%).

Crystallization of the faintly yellow colored syrupy Compound No. 3 (569.0 mg) from a mixed solvent of benzene and n-hexane gave 478.4 mg of Compound No. 3 as colorless needles.

(c) Synthesis of 6-azido-3,6-dideoxy-3-fluoro-1,2-O-isopropylidene-α-D-glucofuranose (Compound No. 4)

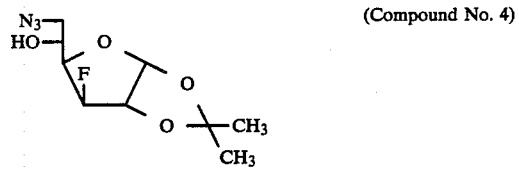

(Compound No. 4)

The syrupy Compound No. 3 (33.60 g) obtained in the above procedure (b) was dissolved in 600 ml of dry dimethylformamide (DMF), to which was then added 6.96 g of sodium azide. The mixture obtained was heated at 120° C. for 1 hour under stirring to effect the reaction for replacing the 6-tosyloxy group by an azido group. The orange-yellow colored uniform reaction solution as formed was concentrated and the resultant brown colored residue was dissolved in 2.5 l of chloroform. The solution in chloroform was washed with water, dried over anhydrous sodium sulfate and then concentrated to give a lightly brown colored syrup. This syrupy material was purified by silica gel column chromatography on a column of 500 ml of silica gel (as developed with benzene-ethyl acetate (6:1) as eluent) to give the titled Compound No. 4 as a colorless syrup. Yield 21.7 g (98%).

(d) Synthesis of methyl 6-azido-3,6-dideoxy-3-fluoro-α- and β-D-glucopyranosides (Compound No. 5)

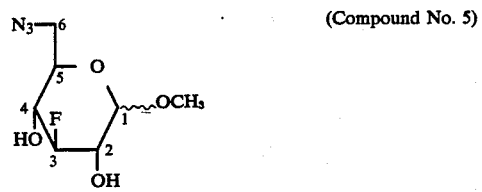

(Compound No. 5)

Compound No. 4 (531.2 mg) obtained in the above procedure (c) was dissolved in 30 ml of dry methanol and the methanolic solution obtained was then admixed with 2.7 g of an ion-exchange resin, "Amberlite" CG-120 (H-cycle) which had been impregnated with methanol. The whole mixture obtained was heated for 30 hours under refluxing of the methanol, and the mixture was filtered to remove the resin. The filtrate obtained was concentrated to give a lightly yellow colored syrup, which was then purified by silica gel column chromatography on a column of 20 ml of silica gel (as developed with chloroform-methanol (8:1) as eluent). There was afforded 470 mg of the titled Compound No. 5 as a colorless syrup. Yield 99%.

This Compound No. 5 was examined by determination of its $^1$H-N.M.R. (250 MHz), when it was observed that this compound No. 5 comprised a mixture of the α-isomer and the β-isomer at a molar ratio of 1:2.

(e) Synthesis of methyl 6-azido-2,4-di-O-benzyl-3,6-dideoxy-3-fluoro-α- and β-D-glucopyranosides (Compound No. 6)

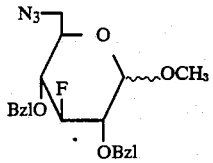
(Compound No. 6)

where Bzl denotes a benzyl group herein and hereinafter, unless otherwise stated.

Compound No. 5 (250.0 mg) obtained in the above procedure (d) was dissolved in 5 ml of dry DMF, to which were then added 317 mg of finely pulverized solid potassium hydroxide and then 0.39 ml of benzyl chloride. The whole mixture obtained was stirred at room temperature for 1 hour, and the resulting reaction mixture in the form of a suspension was filtered to remove the insoluble solids. The insoluble solids were washed with DMF and the DMF washing was added into the filtrate, which was then concentrated to give a syrupy material. This syrup was purified by silica gel column chromatography on a column of 45 ml of silica gel (as developed with chloroform-benzene (1:1) as eluent) to afford the titled Compound No. 6 as a colorless syrup. Yield 418 mg (90%).

(f) Synthesis of 1-O-acetyl-6-azido-2,4-di-O-benzyl-3,6-dideoxy-3-fluoro-α- and β-D-glucopyranoses (Compound No. 7)

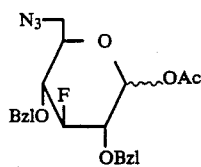
(Compound No. 7)

where Ac denotes an acetyl group.

Compound No. 6 (253.5 mg) obtained in the above procedure (e) was dissolved in 1.25 ml of acetic anhydride, which was then cooled to −20° C. and admixed with 0.0125 ml of sulfuric acid. The mixture so obtained was stirred at −20° C. overnight (for 19 hours) to effect the acetylation. The resulting reaction solution was poured into 100 ml of chloroform, and the resulting solution was washed with aqueous 5% sodium hydrogen carbonate and then with water, dried over anhydrous sodium sulfate and concentrated.

The yellow colored syrup so obtained was purified by silica gel column chromatography in a column of 12 ml of silica gel (as developed with chloroform alone as eluent) to afford the titled Compound No. 7 as a colorless syrup. Yield 228 mg (84%).

(g) Synthesis of 6-azido-2,4-di-O-benzyl-3,6-dideoxy-3-fluoro-α-D-glucopyranosyl bromide (Compound No. 8)

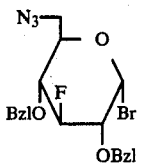
(Compound No. 8)

where Bzl stands for a benzyl group.

Compound No. 7 (1.60 g) obtained in the above procedure (f) was taken up into 31 ml of dry dichloromethane, to which was then added 1.71 g of titanium tetrabromide. The mixture obtained was stirred at room temperature for 1 hour to effect the bromination. The reaction mixture in the form of a red colored suspension was diluted with 300 ml of dry toluene, mixed with 16 g of anhydrous sodium acetate and then stirred for 3 hours. During this, the reaction mixture was changed from the state of a red colored suspension into a lightly yellow colored syrup. The reaction mixture was then filtered and the filtrate was concentrated to give a lightly yellow colored syrup. This syrup was purified by silica gel column chromatography on a column of 100 ml of silica gel (as developed with chloroform alone as eluent) to afford the titled Compound No. 8 as a colorless syrup. Yield 506 mg (30%). $[\alpha]_D^{25} + 193°$ (c 1, chloroform).

Infrared absorption spectrum: 2110 cm$^{-1}$ (azido).

$^1$H-N.M.R. spectrum (in deutero-chloroform, with tetramethylsilane as internal standard): δ 4.99 (1H dt, H-3), 6.31 (1H t, H-1), $^3J_{1,2}=4.0$, $^3J_{2,3}=9.0$, $^3J_{3,4}=8.5$, $^4J_{1,F}=4.0$, $^3J_{2,F}=12$, $^2J_{3,F}=53.0$, $^3J_{4,F}=14.0$ Hz.

EXAMPLE 2

Synthesis of 6-O-(2'-O-benzyl-3'-benzyloxycarbonylamino-4',6'-O-cyclohexylidene-3'-deoxy-α-D-glucopyranosyl)-1,3-bis-N-benzyloxycarbonyl-2-deoxystreptamine (Compound No. 10) from 6-O-(2'-O-benzyl-3'-benzyloxycarbonylamino-3'-deoxy-α-D-glucopyranosyl)-1,3-bis-N-benzyloxycarbonyl-2-deoxystreptamine (Compound No. 9)

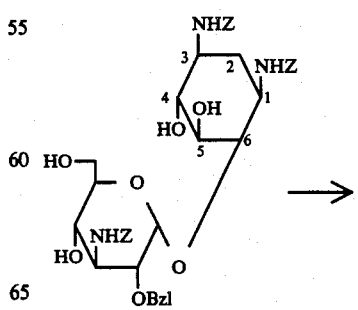
(Compound No. 9)

-continued

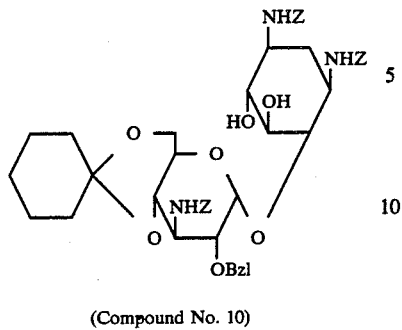

(Compound No. 10)

where Z denotes a benzyloxycarbonyl group and Bzl denotes a benzyl group herein and also hereinafter, unless otherwise stated.

Compound No. 9 of the formula as above (247.0 mg) (see S. Umezawa, K. Tatsuta and S. Koto "Bull. Chem. Soc. Jpn." 42, 533–537 (1969)) was dissolved in 3.5 ml of dry DMF, to which were added 10.6 mg of p-toluenesulfonic acid and then 0.05 ml of 1,1-dimethoxycyclohexane. The mixture so obtained was stirred at 60° C. for 1 hour under reduced pressure of 20 to 25 mm Hg, and to the resulting reaction mixture was added further 0.007 ml of 1,1-dimethoxycyclohexane, followed by effecting the reaction for introduction of the 4,6-O-cyclohexylidene group for 1 hour under the same reaction conditions as above.

The resulting reaction solution was mixed with 100 ml of aqueous 5% sodium hydrogen carbonate to deposit a precipitate which was then removed by filtration. The precipitate separated was purified by silica gel column chromatography in a column of 40 ml of silica gel (as developed with chloroform-methanol (10:1) as eluent) to give the titled Compound No. 10 as a colorless solid. Yield 156.7 mg (58%). $[\alpha]_D^{25} +40°$ (c 1, N,N-dimethylformamide).

EXAMPLE 3

(a) Synthesis of 6'-azido-2',4',2"-tri-O-benzyl-1,3,3"'-tris-N-(benzyloxycarbonyl)-4",6"-O-cyclohexylidene-3',6'-deamino-3'-deoxy-3'-fluorokanamycin A (Compound No. 11)

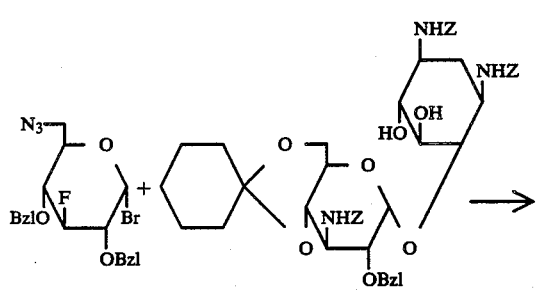

-continued (Compound No. 11)

Compound No. 8 as obtained in the procedure of Example 1, (g), namely 6-azido-2,4-di-O-benzyl-3,6-dideoxy-3-fluoro-α-D-glucopyranosyl bromide (419.1 mg) was dissolved in 3.0 ml of dry dichloromethane, and the resulting solution was mixed with 1.0 g of pulverized "Drierite" (a calcium sulfate), 470.0 mg of pulverized mercuric cyanide and 416.9 mg of Compound No. 10 of Example 2, namely 6-O-(2'-O-benzyl-3'-benzyloxycarbonylamino-4',6'-O-cyclohexylidene-3'-deoxy-α-D-glucopyranosyl)-1,3-bis-N-benzyloxycarbonyl-2-deoxystreptamine to form a mixture as a liquid suspension. This mixture was stirred in a sealed tube in dark at 100° C. overnight (for 12 hours) to effect the condensation of Compound No. 8 with Compound No. 10. After a thin layer chromatographic test of the reaction mixture confirmed that Compound No. 8 had been consumed completely in the reaction mixture, the reaction mixture as the suspension was diluted with 200 ml of dichloromethane and then filtered with aid of a filtration-aid, Celite. The filtrate obtained was washed with aqueous 5% sodium hydrogen carbonate and then with water, dried over anhydrous sodium sulfate and subsequently concentrated to leave a brown colored syrup and a brown colored solid. These products were subjected to a silica gel column chromatography in a column of 70 ml of silica gel (as developed with chloroform-ethyl acetate (3:1) as eluent) for the purpose of isolating and purifying the product, and there was obtained the titled Compound No. 11 as a colorless solid. Yield 89.8 mg (15.3%).

(b) Synthesis of 3'-fluoro-3'-deoxykanamycin A (Compound No. 12)

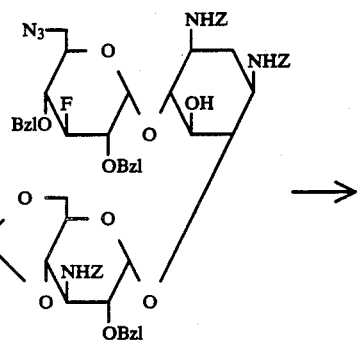

(Compound No. 11)

-continued

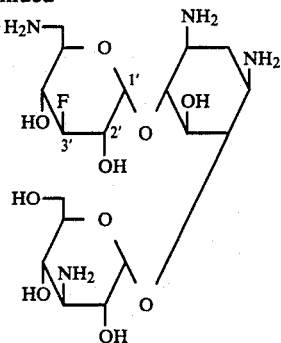

(Compound No. 12)

Compound No. 11 (83.5 mg) as obtained in the above procedure (a) was dissolved in 10 ml of a mixture of water and acetic acid (1:4 by volume), which was then stirred at 80° C. for 1 hour to effect the removal of the cyclohexylidene group from Compound No. 11. The reaction solution became uniform in about 10 minutes of the stirring and then changed into a white-colored, milk-like suspension after 1 hour of the reaction. This reaction mixture as the suspension was concentrated by evaporation of the solvent to give 77.5 mg of a colorless solid comprising 6'-azido-2',4',2''-tri-O-benzyl-1,3,3''-tris-N-(benzyloxycarbonyl)-3',6'-dideoxy-3'-fluorokanamycin A as an intermediate product.

This solid was taken up into 30 ml of a mixture of water and dioxane (1:2 by volume), to which was added 0.10 ml of acetic acid. The whole mixture obtained was subjected to catalytic reduction with hydrogen at ambient temperature in the presence of palladium-black catalyst to effect the reductive conversion of the azido group into the amino group and also concurrently the removal of the benzyl groups and the benzyloxycarbonyl groups from said intermediate product compound. The reaction mixture was filtered to remove the catalyst therefrom, and the filtrate obtained was concentrated. The residual solid was dissolved in water and the aqueous solution was passed into a column of 10 ml of a gel-filtration agent, CM-Sephadex C-25 (a product of Pharmacia Fine Chemicals Co., Sweden), and this column of CM-Sephadex C-25 was eluted gradiently with 0→0.15N aqueous ammonia, with the concentration of ammonia in the eluent being increased gradiently. The eluate was collected in 5 ml-fractions, and every fraction was tested for coloration with ninhydrin. The active fractions containing the desired Compound No. 12 were combined together (totally 60–75 ml) and concentrated to dryness. There was obtained 22.0 mg of Compound No. 12, namely 3'-fluoro-3'-deoxykanamycin A as a colorless solid having no indefinite melting point. $[\alpha]_D^{25} + 116°$ (c 0.5, water).

$^1$H-N.M.R. spectrum (in 20% deutero-ammonia in deutero-water, with tetramethylsilane as internal standard): δ 4.58 (1H dt, H-3'), 5.38 (1H t, H-1'), $^3H_{1',2'} = \sim 4$ Hz, $^4J_{1',F} = \sim 4$ Hz, $^2J_{3',F} = 54.0$ Hz, $^3J_{2',3'} = {^2J_{3',4'}} = 9.0$ Hz.

What we claim is:
1. 3'-Fluoro-3'-deoxykanamycin A of the formula

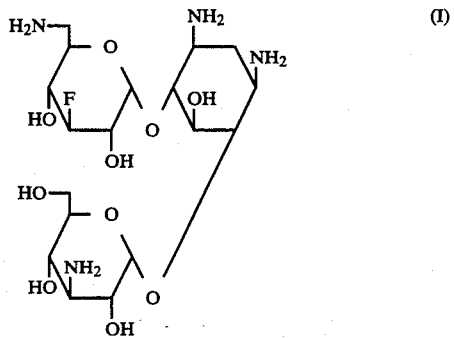

(I)

and a pharmaceutically acceptable acid addition salt thereof.

2. An antibacterial composition comprising an antibacterially effective amount of 3'-fluoro-3'-deoxykanamycin A as defined in claim 1 or a pharmaceutically acceptable acid addition salt thereof as the active ingredient, in association with a pharmaceutically acceptable carrier for the active ingredient.

* * * * *